United States Patent [19]
Dabovic

[11] Patent Number: 6,107,100
[45] Date of Patent: Aug. 22, 2000

[54] COMPOUNDS AND METHODS FOR DETERMINATION OF THIOLS

[75] Inventor: Milan Dabovic, Novi Beograd Serbia, Yugoslavia

[73] Assignee: MetaQuant Trust, Fullerton, Calif.

[21] Appl. No.: 09/079,436

[22] Filed: May 15, 1998

[30] Foreign Application Priority Data

Apr. 30, 1998 [YU] Yugoslavia ............................ P-196/98

[51] Int. Cl.⁷ .................................................. G01N 33/52
[52] U.S. Cl. .......................... 436/119; 436/120; 436/164; 422/56
[58] Field of Search ..................... 436/119, 123, 436/164, 120, 121, 122, 166; 422/56, 61, 68.1, 55, 69, 70

[56] References Cited

U.S. PATENT DOCUMENTS

| | | | |
|---|---|---|---|
| 4,414,414 | 11/1983 | Novak | 436/120 X |
| 4,543,336 | 9/1985 | Westup | 436/122 |
| 5,149,661 | 9/1992 | Gjerde et al. | 422/69 X |
| 5,397,710 | 3/1995 | Steinman | 422/56 X |

FOREIGN PATENT DOCUMENTS 138410  9/1986  Poland .

OTHER PUBLICATIONS

Leeuwenkamp et al. Specific cation effect in the reaction of nitroprusside with cysteine, acetophenone and sulfite (Legal and Boedeker reaction), Pharmaceutisch Weekblad Scientific Edition, vol. 6, pp. 195–202, 1984.

Leeuwenkamp, O.R. et al. "Specific cation effect in the reaction of nitroprusside with cysteine, acetophenone and sulfite (Legal and Boedeker reaction)", Pharm. Weekbl., Sci. Ed., 6(5), pp. 195–202, 1984.

*Primary Examiner*—Elizabeth McKane
*Attorney, Agent, or Firm*—Robert D. Fish; Fish & Associates, LLP

[57] ABSTRACT

Compositions and methods are provided for determining thiols or disulphides in which a sulfur containing analyte is combined with a thiol-specific reagent to produce an intermediate, and the intermediate is combined with a solvent insoluble compound to produce a solid state complex. In one aspect of preferred embodiments the intermediate comprises a chromophore, and in especially preferred embodiments the chromophore is detectable with the naked eye. In another aspect of preferred embodiments the thiol-specific reagent comprises a nitroso-donor, and more preferably Na-nitroprusside. In yet another aspect of preferred embodiments, the solvent insoluble compound comprises a basic or acidic metallic compound, or a polymeric matrix. Still more preferred solvent insoluble compounds comprise Zn-hydroxide, Ni-hydroxide or Al-hydroxide. These compositions and methods are more sensitive and reliable method than that previously available, especially for the determination of homocysteine.

14 Claims, 4 Drawing Sheets

Photo 1
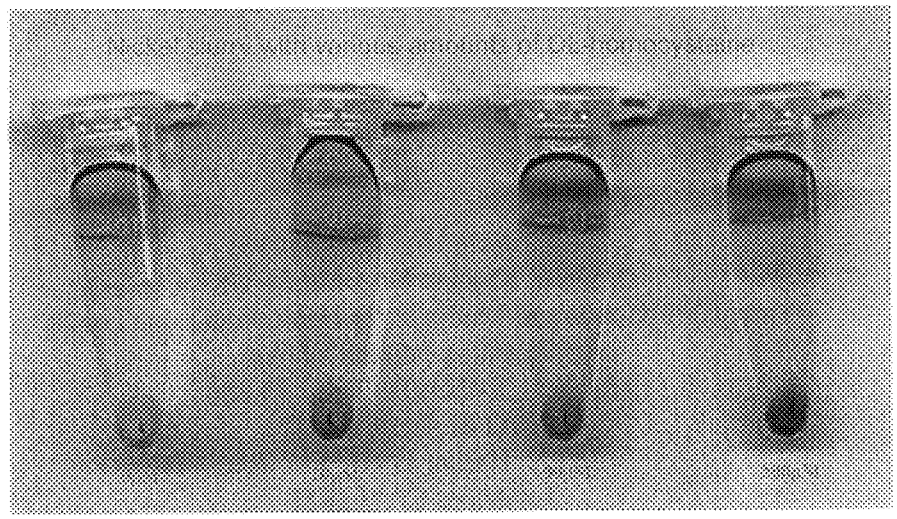
Photo 2
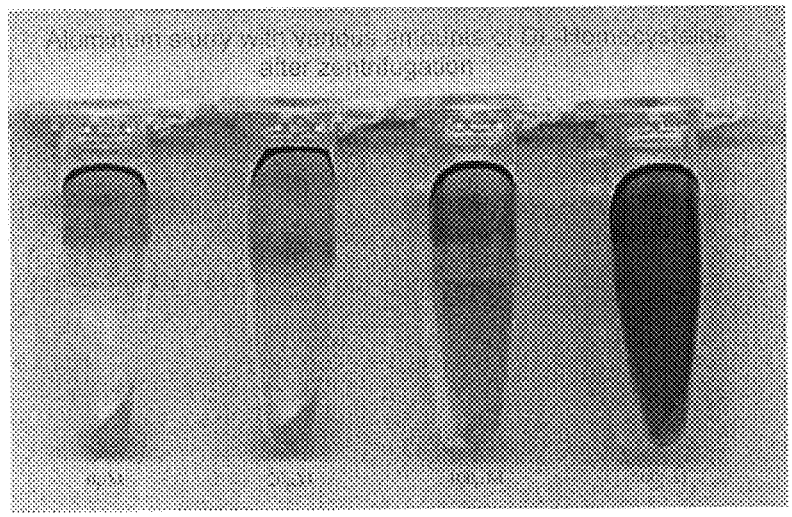
Photo 3
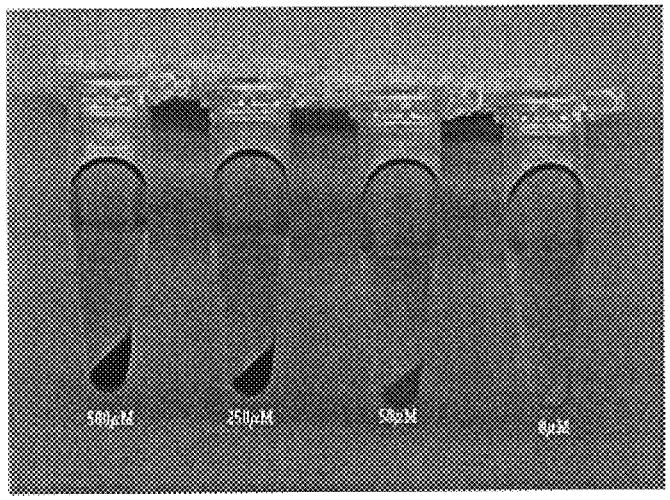

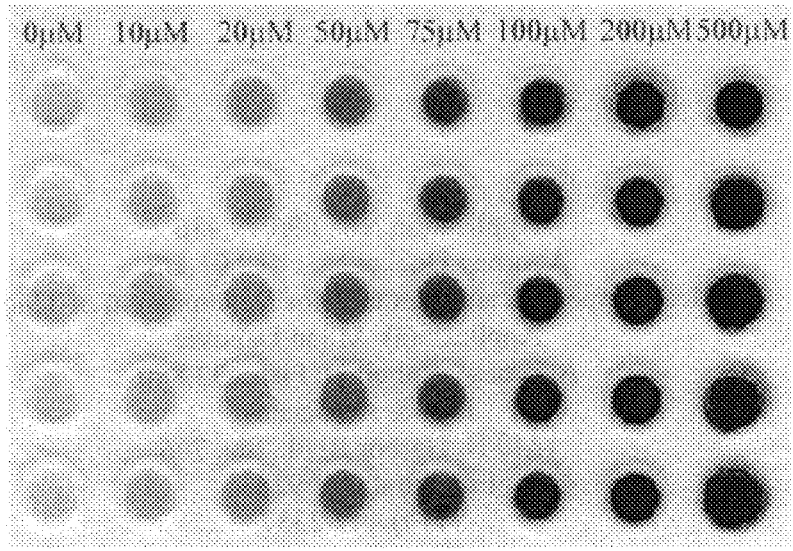
Photo 4
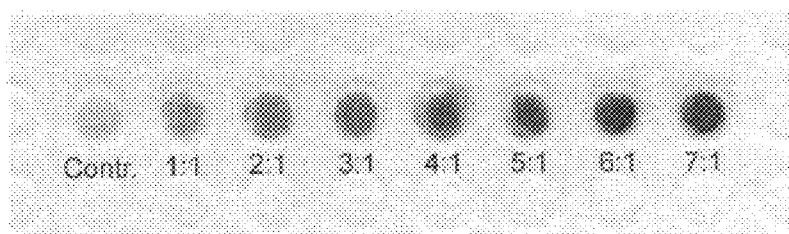
Photo 5
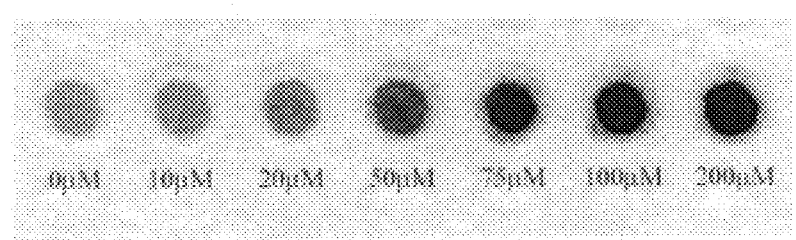
Photo 6
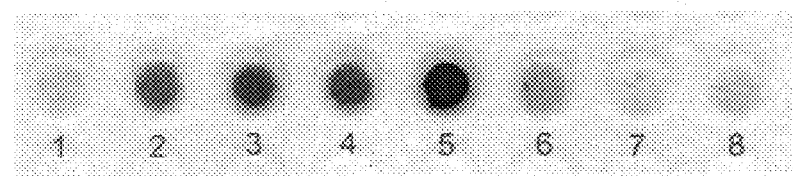
Photo 7

COMPOUNDS AND METHODS FOR DETERMINATION OF THIOLS

FIELD OF INVENTION

The present invention relates to the field of analytical chemistry and biochemistry of sulfur compounds.

BACKGROUND

The occurrence of sulfur containing compounds is ubiquitous in the biotic and abiotic environment. Oftentimes, numerous sulfur-containing compounds are hazardous to, or have important functions in biological systems.

Of special importance is the monitoring of levels of specific sulfur containing com-pounds in biological fluids (e.g. blood, urine, serum, etc.). Specifically, two sulfur containing amino acids, homocysteine and cysteine, are of increasing importance due to their main contribution to several severe human diseases such as occlusive cardiovascular diseases or metabolic disorders which manifest themselves in hypercystinuria, cystinlithiasis or hyperhomocystinuria.

Present methods of detection and quantitation of sulfur containing compounds are laborious and expensive and have to be performed by specialized clinical laboratories using oftentimes expensive reagents and equipment. By their very nature, contemporary assays can not be routinely performed as so called home-tests. Therefore, patients are reluctant to undergo regular monitoring of these specific sulfur-containing compounds due to both cost and inconvenience.

Currently used analytical methods encompass derivatizing and HPLC, GC-MS, ELISA-type assays and simple spectrophotometric procedures (1–7).

Of special importance are two common inherited pathological states, namely homo-cystinuria and cystinuria. Homocystinuria is characterized by increased concentrations of homocystine/homocysteine in blood and urine. Genes involved in this metabolic disorder are coding for Cystathionine-β-synthase—a key enzyme in the transsulfuration pathway that converts methionine to cysteine. The other forms of hyperhomocystinuria are the result of impaired conversion of homocysteine to methionine, a reaction catalyzed by the homocysteine: methyltetrahydrofolate methyltransferase and two essential cofactors, methyltetrahydrofolate and methylcobalamin. Although the homozygous type of this inherited disease is relatively rare, the heterozygous type occurs more frequently and is usually discovered by methionine loading tests. Despite the presence of sophisticated and complex procedures, in current clinical practice one uses still an old, colorimetric cyanide-nitroprusside test as the simplest way of demonstrating an increased excretion of sulfur containing compounds in urine. The major disadvantage of this currently most used method is it's insensitivity and extreme instability of the developed color.

Of even greater importance is cystinuria, a pathological state of increased cystine level in urine, which is essentially an inherited defect of membrane transport in kidneys. Cystinuria is the most common inherited defect in amino acid transport and is characterized by impaired tubular reabsorption and excessive excretion of amino acids, especially cysteine. Since cystine is the least water soluble of the natural occurring amino acids, its overexcretion predisposes to the formation of renal, urethral and bladder stones. Such stones are responsible for the signs and symptoms of the disorder. Again, there are homozygous as well as heterozygous cystinurics. Remarkably, the frequency of homozygous cystinuria is about 11:10.000. Cystine stones account to 1–2% of all urinary calculi and are the most common cause of stones in children. Current medical literature advises to screen all urinary tract stone patients for elevated cystine level in urine. For that purpose, again the nitroprusside test is the most favorable and is routinely performed on all patients with urolithiasis to exclude the diagnosis of cystinuria. Cystinuria patients are treated with a variety of drugs (Bicarbonate, polycitrate, ascorbic acid, etc.) and need frequent monitoring of their urinary cysteine to adjust the proper dosage of drugs and to prevent the recurrence of urolithiasis. With these facts in mind, the need for a reliable home test is obvious. Unfortunately, a reliable and simple home test is not available on the over the counter market. In short, there is a need to provide a new, reliable and sensitive test for cystine, homocystine or other thiols in biological fluids.

SUMMARY OF THE INVENTION

The present invention is directed towards compositions and methods of determining thiols or disulphides in which a sulfur containing analyte is combined with a thiol-specific reagent to produce an intermediate, and the intermediate is combined with a solvent insoluble compound to produce a solid state complex.

In one aspect of preferred embodiments the intermediate comprises a chromophore, and in especially preferred embodiments the chromophore is detectable with the naked eye. In another aspect of preferred embodiments the thiol-specific reagent comprises a nitroso-donor, and more preferably Na-nitroprusside. In yet another aspect of preferred embodiments, the solvent insoluble compound comprises a basic or acidic metallic compound, or a polymeric matrix. Still more preferred solvent insoluble compounds comprise Zn-hydroxide, Ni-hydroxide or Al-hydroxide.

These compositions and methods are more sensitive and reliable method than that previously available, especially for the determination of homocysteine.

Various objects, features, aspects and advantages of the present invention will become more apparent from the following detailed description of preferred embodiments of the invention, along with the accompanying drawings in which like numerals represent like components.

BRIEF DESCRIPTION OF FIGURES AND PHOTOS

FIG. 1: UV/VIS absorption spectrum of the EDTA-dissolved $Zn(OH)_2$-homocysteine-nitroprusside complex FIG. 2: Graph describing the dependence of absorption to concentration of the monitored thiol over time FIG. 3: Graph describing the dependence of slopes from graph 2 to the centration of the monitored thiol.

Photo 1: Pellet of a water insoluble, basic Ni-compound with various amounts of homocysteine.

Photo 2: Pellet of a water insoluble, basic Al-compound with various amounts of homocysteine.

Photo 3: Pellet of a water insoluble, basic Zn-compound with various amounts of homocysteine.

Photo 4: Concentration dependent color intensity of a water insoluble, basic Zn compound with various amounts of homocysteine.

Photo 5: Mixtures of constant amounts of a water insoluble, basic Zn-compound with different volumes of solutions of constant amounts of homocysteine.

Photo 6: Mixtures of constant amounts of a water insoluble, basic Zn-compound with different volumes of solutions of constant amounts of homocysteine, formed by reduction with a constant amount of TCEP.

Photo 7: Mixtures of constant amounts of a water insoluble, basic Zn-compound with constant amounts of various thiols including negative control.

DETAILED DESCRIPTION

Figure 1:
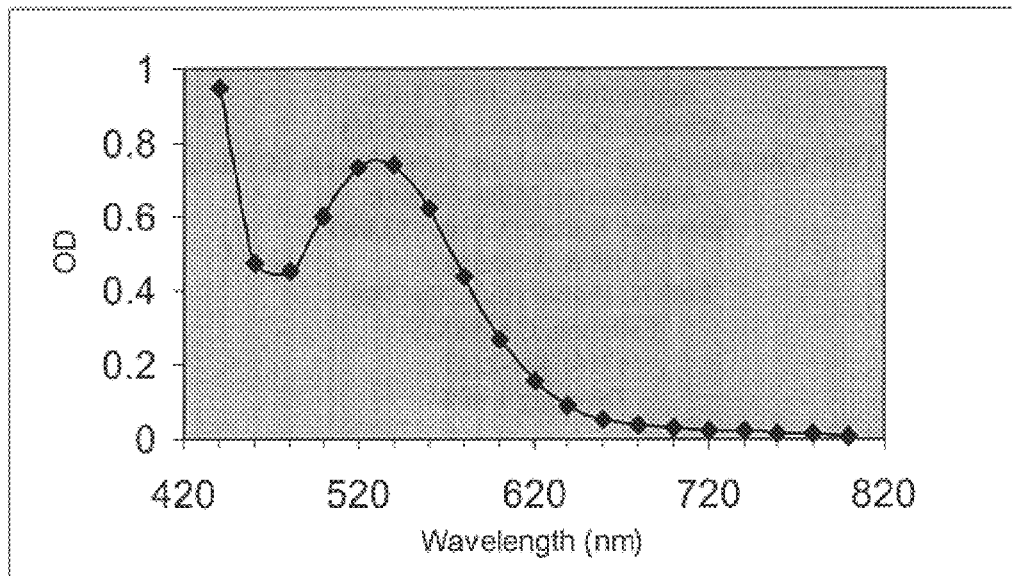

As used herein the terms "determine" and "determination" means quantitative and/or qualitative analysis.

Also as used herein, the term "solvent insoluble" compound refers to compounds which are insoluble in the solvent being used. The solvent of choice will often be water due to its low cost, easy handling and low toxicity. However, other solvents may be used, including ordinary alcohols such as methanol and ethanol, as well as aprotic solvents such as dimethylformamide and dimethylsulfoxide, and even mixtures of solvents such as water and acetone.

Preferred solvent insoluble compounds are those which can immobilize and thereby stabilize an intermediate. Examples are precipitated or dispersed metallic hydroxides, insoluble salts such as basic phosphates, carbonates, citrates, and silica. It is especially preferred to provide the insoluble compounds as slurries, such as may be prepared by mixing water soluble metallic salts with equimolar amount or excess of alkaline metal hydroxide, preferably in the presence of other ions (e.g. citrate). Such slurries have been described in the chemical literature and several of those have found a practical application in chemical analysis. A recent example of using a water insoluble, basic Zn-compound is described by K. Shanti and N. Balasubramanian (8). The authors prepared practically an $H_2S$ trapping solution with insoluble basic Zn-slurry, which they described as "Zinc acetate-citrate-sodium hydroxide trapping solution". This solution was used to concentrate $H_2S$ as an air-pollutant from various sources and the method was claimed to be very sensitive for $H_2S$ determination in air by using bromate and 2,7-dichlorofluorescein.

Recently, several papers were published covering the use of a long-known thiol-specific reagent (Na-nitroprusside) for qualitative and quantitative measurement of urinary cystine and homocystine levels. Such tests are known to be useful in monitoring cysteine levels in patients with cystinuria and cystinlithiasis (9–11). In these references, the authors used NaCN for disulfide reduction and Na-nitroprussside as a reagent and $NaCO_3$ as a basic co-reagent. Although well characterized and established in clinical routine procedures, these methods suffer from several disadvantages: first, the developed color is highly unstable (cysteine several minutes, homocysteine immediate degradation), second, NaCN is a highly toxic compound and finally, the method is insensitive to levels lower than 500 $\mu M$ of the thiol compound.

Quite unexpectedly, I discovered that a combination of water insoluble, basic Zn-compounds, Na-nitroprusside and thiol or reduced disulfide develop an unusually stable and intense color that can be detected at very low concentrations. (see photographs 1–3). This, in turn, allows an additional and substantial amplification by means of filtration or centrifugation (see photographs 3 and 4). The developed color in such compounds are stable for at least 24 hrs at room temperature, and the concentration dependent color intensity is reproducible over a wide range of concentrations (see photo 4).

In further experimentation I discovered that other insoluble compounds can be used instead of the originally discovered Zn compounds. Examples include other metallic compounds such as aluminum hydroxide, tin hydroxide, titanium hydroxide, as well as non-metallic compounds such as silica. I also discovered that these compounds need not be basic, and for example, titanium hydroxide and silica are both acids which will work nicely. In general, and while not limiting ourselves to a particular theory, it is contemplated that preferred insoluble compounds will spontaneously form a polymeric structure or other matrix, which prevents or limits the ability of a chromophore or other marker to decompose in homogeneous solution.

To clarify matters, the term "solid state complex" as used herein means a solvent insoluble species carrying a characteristic chemical group such as a chromophore, isotope or a detectable functional group. The characteristic group may be located on the surface, or buried inside the complex. Still further, solid state complexes as contemplated herein may be crystalline, amorphous or partially crystalline and partially amorphous.

Still further I discovered that other compounds can substitute for Na-nitroprusside. Preferred alternatives include Na nitrite, nitrite esters, and other nitrosodonors.

Even further, I discovered that the compounds and processes disclosed herein are applicable to other thiols besides homocysteine. (see photo 7). Such thiols include cysteine, cystine, alpha-mercapto acetic and alpha-mercapto proprionic acid, mercaptoethanol, glutathione, as well as thiols in petroleum products.

In detecting and quantifying disulfides, which is of great importance in the case of cystinuria or homocystinuria, a variety of reducing agents can be used which do not interfere with the final results (see photo 6). Particularly suitable for this purpose is TCEP ("Molecular Probes"), but other reagents such as $NaBH_4$ or Zn/HCl could be used as well.

The compounds and methods disclosed herein have considerable utility. One particular application is an at-home test kit for detection, treatment and follow-up of a disease characterized by a thiol product or by-product, e.g. cystinuria or cystinlithiasis. Another contemplated application is detection and concentration of sulfur isotope labeled compounds.

However, my invention is not limited to color determination in solid phase; it also can be adopted e.g. for quantitative determination of thiols after re-dissolving the colored pellet in a complexing agent such as EDTA, and then reading the intensity of the developed product using an appropriate reader. For the particular experiments recited below, the product developed a color which was readable at 530 nm (see FIGS. 1–3).

Examples

FIG. 1 shows the absorption spectrum of an EDTA dissolved pellet: To 1.0 ml of a 100 $\mu M$ DL-homocysteine solution, 300 $\mu l$ of the Zn-slurry containing 2.5% Na-nitroprusside were added. After mixing the solution, a brief centrifugation step at 13,000 rpm for 30s was performed and the supernatant discarded. The pellet was dissolved in 0.5M EDTA pH8.0 and immediately scanned in a spectrophotometer between 440 nm and 800 nm. Data were collected every 20 nm. Absorption was plotted versus wavelength.

Figure 2:
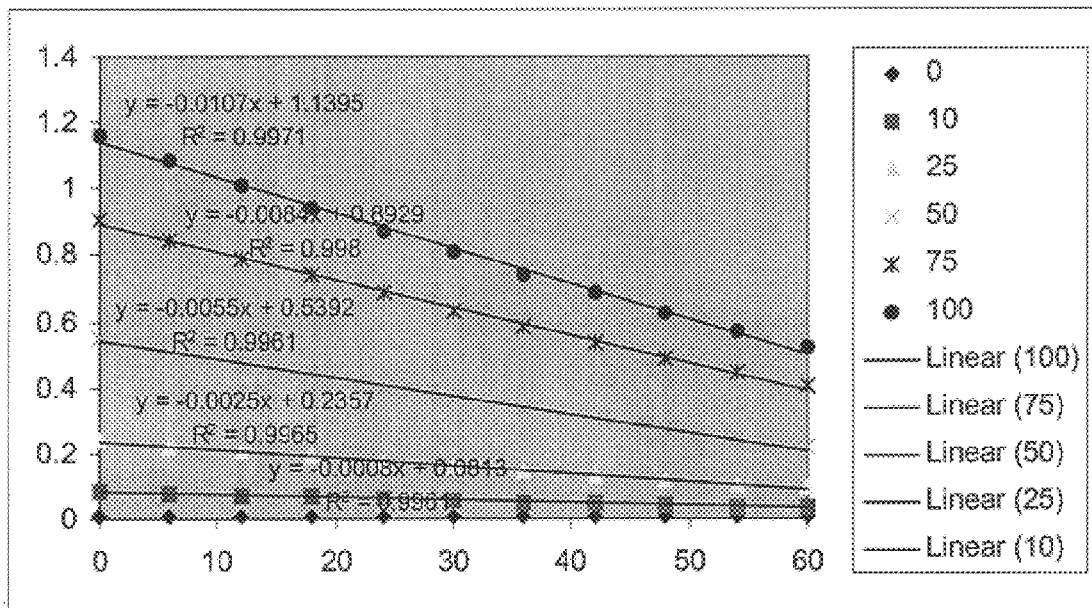

FIG. 2 shows decay of absorbance in dependence of DL-homocysteine concentration: 6 samples containing 1.0 ml of an aqueous solution with various amounts of DL-homo-cysteine (as indicated between 0 and 100 $\mu M$) were mixed with 300 $\mu l$ Zn-slurry containing 2.5%

Na-nitroprusside and vortexed. After mixing the solution, a brief centrifugation step at 13,000 rpm for 30s was performed and the supernatant discarded. The pellet was dissolved in 0.5M EDTA pH8.0 and the absorption immediately read at 530 nm. Data were collected every 6s. Curves were fitted using a linear fit applying the least squares method. R2 was calculated for each curve. Absorption was plotted versus time.

Figure 3:
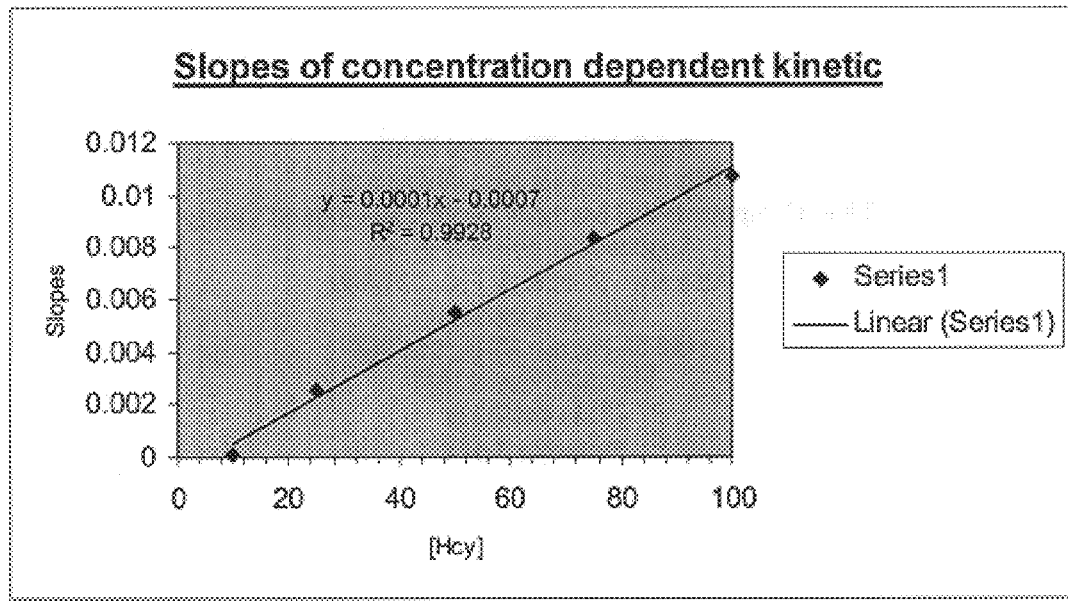

FIG. 3 shows slopes of absorbance decays in dependence of DL-homocysteine concentration: The calculated slopes from FIG. 1 were plotted versus the concentration of DL-homocysteine. The curves was fitted using a linear fit applying the least squares method. R2 was calculated. The slopes were plotted versus the DL-homo-cysteine concentration.

Preparation of a water insoluble, basic metallic compound. General procedure: ~1% aqueous solution of a metallic salt (such as $Zn(AcO)_2$, $CdCl_2$, $NiSO_4$, $Al(AcO)_3$, etc.) is mixed with equimolar amount or a slight excess of NaOH (0.1M) in the presence of ~10–20% mol eq. of $Na_3$Citrate. The NaOH solution is added slowly to the metallic salt—citrate solution at room temperature with continuous stirring, at such a rate, that the insoluble basic metallic compound is gradually formed. The slurry is finely suspended and precipitates only after longer standing. Such metallic compounds are stable over months at room temperature, and slurries should be well shaken each time before use.

Preparation of a water insoluble, basic Zn-slurry: 10 g of Zn(Ac)2 and 2.94 g of $Na_3$Citrate are dissolved in 1000 ml water. NaOH (0.1M) is slowly added under continuous stirring. The slurry is well shaken prior to use.

Preparation of a thiol solution: 100 mM aqueous DL-homocysteine stock solution is prepared. This stock solution is diluted 1:100 to yield a 1 mM DL-homocysteine solution. From this solution, 10 $\mu$l, 20 $\mu$l, 50 $\mu$l, 75 $\mu$l, 100 $\mu$l, 200 $\mu$l and 500 $\mu$l aliquots are pipetted into 1.5 ml eppendorf tubes, respectively, and water was added ad 1.0 ml, respectively. For each concentration, 5 tubes were set up.

Procedure 1 (for thiol determination): To 20 ml of the fresh prepared Zn-slurry, 500 mg Na-nitroprusside were added and the mixture was vortexed until all of the Na-nitroprusside was dissolved. 300 $\mu$l of the so prepared Na-nitroprusside Zn-slurry were added to the previously prepared tubes containing 1 ml of the homocysteine solution. The color develops immediately. After thoroughly mixing, 1.0 ml of the mixture was filtered onto Whatman 3M paper using a vacuum manifold. For documentation, the filter was placed on a flatbed scanner (see photo 4). All preparations and reactions were performed at room temperature. The incubation time of the homocysteine solution with the Na-nitroprusside Zn-slurry was less than 5 min. The developed color remained unchanged after 24 hrs.

Procedure 2 (for disulfide determination): Existing disulfides have to be reduced to the thiol state prior to determination. For this purpose, a 10 mM TCEP solution in water is prepared and 10%($^{vol}/_{vol}$) of this solution is added to the solution containing the disulfide. After thoroughly mixing, the procedure is identical to procedure 1.

While not limiting ourselves to nitroso donor reagents (such as nitroprusside) as a means of thiol determination, other means of thiol determination are also contemplated (such as radio isotopes, fluorescent, phosphorescent or chemoluminescent reagents, etc.). The format of the presented invention can either be in form of a simple home test with or without metabolic challenge (methionine loading test), but can also be applied in a clinical chemistry laboratory as a qualitative assessment of thiol compounds in fluids. As used herein, the term "determining" includes both qualitative and quantitative determination of the thiol compound.

Thus, specific embodiments and applications of thiolspecific reagents and water insoluble metallic preparations have been disclosed. It should be apparent, however, to those skilled in the art that many more modifications besides those already described are possible without departing from the inventive concepts herein. For example, modified non-metallic water insoluble matrices (as silica gel, e.g.) can be used in aqueous and non-aqueous media. Similarly, it is possible to use indirect means of quantitation such as derivatized thiol components that can be detected by a specific reagent and amplified on a solid matrix. The inventive subject matter, therefore, is not to be restricted except in the spirit of the appended claims.

Photographs

Photo 1: Pellets of Ni-slurry with various concentrations of DL-homocysteine: To 4 samples containing 1.0 ml of an aqueous solution with various amounts of DL-homocysteine (as indicated between 0 and 500 $\mu$l) were mixed with 300 $\mu$l Ni-slurry containing 2.5% Na-nitroprusside and vortexed. After mixing the solution, a brief centrifugation step at 13,000 rpm for 30s was performed. Pellets were immediately captured on a flatbed scanner.

Photo 2: Pellets of Al-slurry with various concentrations of DL-homocysteine: To 4 samples containing 1.0 ml of an aqueous solution with various amounts of DL-homocysteine (as indicated between 0 and 500 $\mu$l) were mixed with 300 $\mu$l Al-slurry containing 2.5% Na-nitroprusside and vortexed. After mixing the solution, a brief centrifugation step at 13,000 rpm for 30s was performed. Pellets were immediately captured on a flatbed scanner.

Photo 3: Pellets of Zn-slurry with various concentrations of DL-homocysteine: To 4 samples containing 1.0 ml of an aqueous solution with various amounts of DL-homocysteine (as indicated between 0 and 500 $\mu$l) were mixed with 300 $\mu$l Zn-slurry containing 2.5% Na-nitroprusside and vortexed. After mixing the solution, a brief centrifugation step at 13,000 rpm for 30s was performed. Pellets were immediately captured on a flatbed scanner.

Photo 4: Filter with Zn-slurry with various concentrations of DL-homocysteine between 0 and 500 $\mu$l as indicated. To sets of 5 samples containing 1.0 ml of an aqueous solution with various amounts of DL-homocysteine were mixed with 300 $\mu$l Zn-slurry containing 2.5% Na-nitroprusside and vortexed. After mixing the solution, 1.0 ml was filtered onto Whatman 3M filter paper in a vacuum manifold. The filter was dried for ~60 min and then captured on a flatbed scanner.

Photo 5: Filter with Zn-slurry with various amounts of samples containing identical concentrations of DL-homocysteine: To 300 $\mu$l Zn-slurry containing 2.5% Na-nitroprusside various volumes of a solution containing 20 $\mu$M DL-homocysteine were added. The Control was 300 ml water, the remaining dots represent multiple amounts of 300 $\mu$l with constant concentration of DL-homocysteine between 300 $\mu$l (1:1) and 20 $\mu$M (7:1).

Photo 6: Filter with Zn-slurry with samples containing various concentrations of DL-homocysteine in the presence of TCEP: Samples containing 1.0 ml of an aqueous solution with various amounts of DL-homocysteine (as indicated between 0 and 200 $\mu$M) and a final concentration of TCEP of 1 mM were mixed with 300 $\mu$l Zn-slurry containing 2.5% Na-nitroprusside and vortexed. After mixing the solution, 1.0 ml was filtered onto Whatman 3M filter paper in a vacuum manifold. The filter was dried for ~60 min and then captured on a flatbed scanner.

Photo 7: Filter with Zn-slurry with samples containing various thiols: Samples containing 1.0 ml of an aqueous solution with various thiols at a concentration of 200 µM were mixed with 300 µl Zn-slurry containing 2.5% Na-nitroprusside and vortexed. Water was used as a negative control. After mixing the solution, 1.0 ml was filtered onto Whatman 3M filter paper in a vacuum manifold. The filter was dried for ~60 min and then captured on a flatbed scanner. The individual dots are: 1=Water, 2=β-Mercaptoethanol, 3=L-Cysteine, 4=Dithiothreitol, 5=DL-Homocysteine, 6=L-Homocystine, 7=Methionine, 8=$Na_2S$.

References

1. Fiskerstrand, T., Refsum, H., Kvalheim, G and Ueland, P. M., "Homocysteine and other thiols in plasma and urine: Automated Determination and sample stability", Clin. Chem. (1993) 39(2):263–271
2. Turnell, D. C. and Cooper, J. D. H., "Rapid assay for amino acids in serum and urine by pre-column derivatization and reversed-phase liquid chromatography", Clin. Chem. (1982) 28(3):527–531
3. Wronski, M., "Separation of urinary thiols as tributyltin-mercaptides and determination using capillary isotachophoresis", J. Chromatog. B (1996) 676:29–34.
4. Allen, et al., "Assays for sulfhydryl amino acids and methylmalonic acid and their application to diagnosis of cobalamin deficiency", U.S. Pat. No. 5,438,017.
5. Stabler, S. P., Marcell, P. D., Podell, E. R. and Allen, R. H., "Quantitation of total homocysteine, total cysteine and methionine in normal serum and urine using gas chromatography-mass spectrometry", Anal. Biochem. (1987) 162:185–196.
6. Van Atta, et al., "Immunoassay for homocysteine", U.S. Pat. No. 5,478,729.
7. Comprehensive review article concerning spectrophotometry of cysteine/cystine, Chrastil, J., "Spectrophotometric determination of cysteine and cystine in peptides and proteins", Analyst (1989) 114:1133–1136.
8. Shanti, K. and Balasubramanian, N., "Method for sampling and analysis of hydrogen sulfide", Analyst (1996) 121:647–650.
9. Wu, J. T., Wilson, L. R. and Christensen, S., "Conversion of a qualitative screening test to a quantitative measurement of urinary cystine and homocystine", Ann. Clin. Lab. Sc. (1992) 22(1):18–29.
10. Berg, von W and Kilian, O, "Semiquantitativer Cystein-Schnelltest Moglichkeit zur Verlaufkontrolle der Ascorbinsauretherapie bei Cystinurie und Cystinlithiasi", J. Clin. Chem. Clin. Biochem. (1988) 26:223–227.
11. Berg, von W., Kilian, O and Brundig, P., "Einfacher Schnelltest mit Karbonat/Nitroprussid zur semiquantitativen Bestimmung von Zystein im Urin-Moglichkeit einer Verlaufskontrolle unter Askorbinsauretherapie beim Zystinsteinleiden".

I claim:

1. A method of determining a sulfur containing analyte comprising:

combining the analyte with a thiol-specific reagent to produce an intermediate; and intermingling the intermediate with a solvent insoluble compound in a solvent to produce a solid state complex, wherein the solid state complex is stable in the solvent.

2. The method of claim 1 wherein the intermediate comprises a chromophore.

3. The method of claim 1 wherein the thiol-specific reagent comprises a nitroso-donor.

4. The method of claim 3 wherein the thiol-specific reagent comprises Na-nitroprusside.

5. The method of claim 1 wherein the solvent insoluble compound comprises a basic metallic compound.

6. The method of claim 1 wherein the solvent insoluble compound comprises an acidic metallic compound.

7. The method of claim 1 wherein the solvent insoluble compound comprises a polymeric matrix.

8. The method of claim 1 wherein the solvent insoluble compound comprises a compound selected from the group consisting of Zn-hydroxide, Ni-hydroxide and Al-hydroxide.

9. The method of claim 1 wherein the solvent insoluble compound comprises silica.

10. The method of claim 1 wherein the analyte comprises a compound selected from the group consisting of naturally occurring thiols and disulphides.

11. The method of claim 1 wherein the analyte comprises a compound selected from the group consisting of homocysteine, homocystine, cysteine and cystine.

12. The method of claim 1 wherein the intermediate comprises a chromophore, the thiol-specific reagent comprises a nitroso-donor, and the solvent insoluble compound comprises a compound selected from the group consisting of Zn-hydroxide, Ni-hydroxide and Al-hydroxide.

13. The method of claim 12 wherein the analyte comprises a compound selected from the group consisting of homocysteine, homocystine, cysteine and cystine.

14. The method of claim 13 wherein the thiol-specific reagent comprises Na-nitroprusside and the solvent insoluble compound Zn-hydroxide.

* * * * *